United States Patent [19]
Lopez

[11] Patent Number: 5,996,129
[45] Date of Patent: Dec. 7, 1999

[54] GOGGLES

[76] Inventor: Jose A. Lopez, P.O. Box 1163 2895 Old Murphy's Rd., Angels Camp, Calif. 95222

[21] Appl. No.: 09/070,653

[22] Filed: Apr. 30, 1998

[51] Int. Cl.[6] .................................................. A61F 9/02
[52] U.S. Cl. ........................................ 2/431; 2/436; 2/441
[58] Field of Search ............................... 2/431, 433, 436, 2/437, 439, 441, 443

[56] References Cited

U.S. PATENT DOCUMENTS

| | | | |
|---|---|---|---|
| 1,856,879 | 5/1932 | Lufkin | 2/431 X |
| 2,706,815 | 4/1955 | Parmelee | 2/441 |
| 3,505,680 | 4/1970 | Ring | 2/441 X |
| 3,530,506 | 9/1970 | Hoffmaster | 2/441 X |
| 4,831,665 | 5/1989 | Palmaer | 2/433 X |
| 5,631,717 | 5/1997 | Spector | 2/433 X |

FOREIGN PATENT DOCUMENTS

| | | | |
|---|---|---|---|
| 547630 | 9/1942 | United Kingdom | 2/439 |

*Primary Examiner*—Peter Nerbun

[57] ABSTRACT

Goggles for providing interchangeable transparent and mesh screen eye shields on a goggle frame. The device includes a frame shaped to fit on the face of a wearer and having a front and inner and outer surfaces. The inner surface of the frame defines a central space. The ends of a flexible strap are coupled to the frame. The flexible strap is adapted for looping around the back of the head of a wearer to hold the frame to the face of the wearer. A mesh screen eye shield substantially covers the central space at the front of the frame. The mesh screen eye shield has a plurality of generally uniform apertures therethrough. Each of the apertures has a predetermined area and is designed for preventing objects greater than the predetermined sized passing therethrough. The apertures of the mesh screen eye shield are also designed for permitting the passage of moisture therethrough.

1 Claim, 3 Drawing Sheets

GOGGLES

BACKGROUND OF THE INVENTION

1. Field of the Invention

The present invention relates to goggles and more particularly pertains to a new goggles for providing interchangeable transparent and mesh screen eye shields on a goggle frame.

2. Description of the Prior Art

The use of goggles is known in the prior art. More specifically, goggles heretofore devised and utilized are known to consist basically of familiar, expected and obvious structural configurations, notwithstanding the myriad of designs encompassed by the crowded prior art which have been developed for the fulfillment of countless objectives and requirements.

Known prior art goggles include U.S. Pat. No. 4,901,374; U.S. Pat. No. 5,184,354; U.S. Pat. No. 3,104,508; U.S. Pat. No. 4,494,251; U.S. Pat. No. 3,663,959; and U.S. Pat. No. 2,871,642.

While these devices fulfill their respective, particular objectives and requirements, the aforementioned patents do not disclose a new goggles. The inventive device includes a frame shaped to fit on the face of a wearer and having a front and inner and outer surfaces. The inner surface of the frame defines a central space. The ends of a flexible strap are coupled to the frame. The flexible strap is adapted for looping around the back of the head of a wearer to hold the frame to the face of the wearer. A mesh screen eye shield substantially covers the central space at the front of the frame. The mesh screen eye shield has a plurality of generally uniform apertures therethrough. Each of the apertures has a predetermined area and is designed for preventing object, greater than the predetermined size from passing therethrough. The apertures of the mesh screen eye shield are also designed for permitting the passage of moisture therethrough.

In these respects, the goggles according to the present invention substantially departs from the conventional concepts and designs of the prior art, and in so doing provides an apparatus primarily developed for the purpose of providing interchangeable transparent and mesh screen eye shields on a goggle frame.

SUMMARY OF THE INVENTION

In view of the foregoing disadvantages inherent in the known types of goggles now present in the prior art, the present invention provides a new goggles construction wherein the same cain be utilized for providing interchangeable transparent and mesh screen eye shields on a goggle frame.

The general purpose of the present invention, which will be described subsequently in greater detail, is to provide a new goggles apparatus and method which has many of the advantages of the goggles mentioned heretofore and many novel features that result in a new goggles which is not anticipated, rendered obvious, suggested, or even implied by any of the prior art goggles, either alone or in any combination thereof.

To attain this, the present invention generally comprises a frame shaped to fit on the face of a wearer and having a front and inner and outer surfaces. The inner surface of the frame defines a central space. The ends of a flexible strap are coupled to the frame. The flexible strap is adapted for looping around the back of the head of a wearer to hold the frame to the face of the wearer. A mesh screen eye shield substantially covers the central space at the front of the frame. The mesh screen eye shield has a plurality of generally uniform apertures therethrough. Each of the apertures has a predetermined area and is designed for preventing objects greater than the predetermined size from passing therethrough. The apertures of the mesh screen eye shield are also designed for permitting the passage of moisture therethrough.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new goggles apparatus and method which has many of the advantages of the goggles mentioned heretofore and many novel features that result in a new goggles which is not anticipated, rendered obvious, suggested, or even implied by any of the prior art goggles, either alone or in any combination thereof.

It is another object of the present invention to provide a new goggles which may be easily and efficiently manufactured and marketed.

It is a further object of the present invention to provide a new goggles which is of a durable and reliable construction.

An even further object of the present invention is to provide a new goggles which is susceptible of a low cost of manufacture with regard to both materials and labor, and which accordingly is then susceptible of low prices of sale to the consuming public, thereby making such goggles economically available to the buying public.

Still yet another object of the present invention is to provide a new goggles which provides in the apparatuses and methods of the prior art some of the advantages thereof, while simultaneously overcoming some of the disadvantages normally associated therewith. Still another object of the present invention is to provide a new goggles for providing interchangeable transparent and mesh screen eye shields on a goggle frame.

Yet another object of the present invention is to provide a new goggles which includes a frame shaped to fit on the face of a wearer and having a front and inner and outer surfaces. The inner surface of the frame defines a central space. The ends of a flexible strap are coupled to the frame. The flexible strap is adapted for looping around the back of the head of a wearer to hold the frame to the face of the wearer. A mesh screen eye shield substantially covers the central space at the front of the frame. The mesh screen eye shield has a plurality of generally uniform apertures therethrough. Each of the apertures has a predetermined area and is designed for preventing objects greater than the predetermined sized passing therethrough. The apertures of the mesh screen eye shield are also designed for permitting the passage of moisture therethrough.

Still yet another object of the present invention is to provide a new goggles that provides a mesh screen eye shield that provides protection to the eyes of a wearer while still permitting visibility therethrough and eliminating problem of eye shields fogging up from ambient moisture.

Even still another object of the present invention is, to provide a new goggles that does not suffer from the problems of smudged eye shields.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
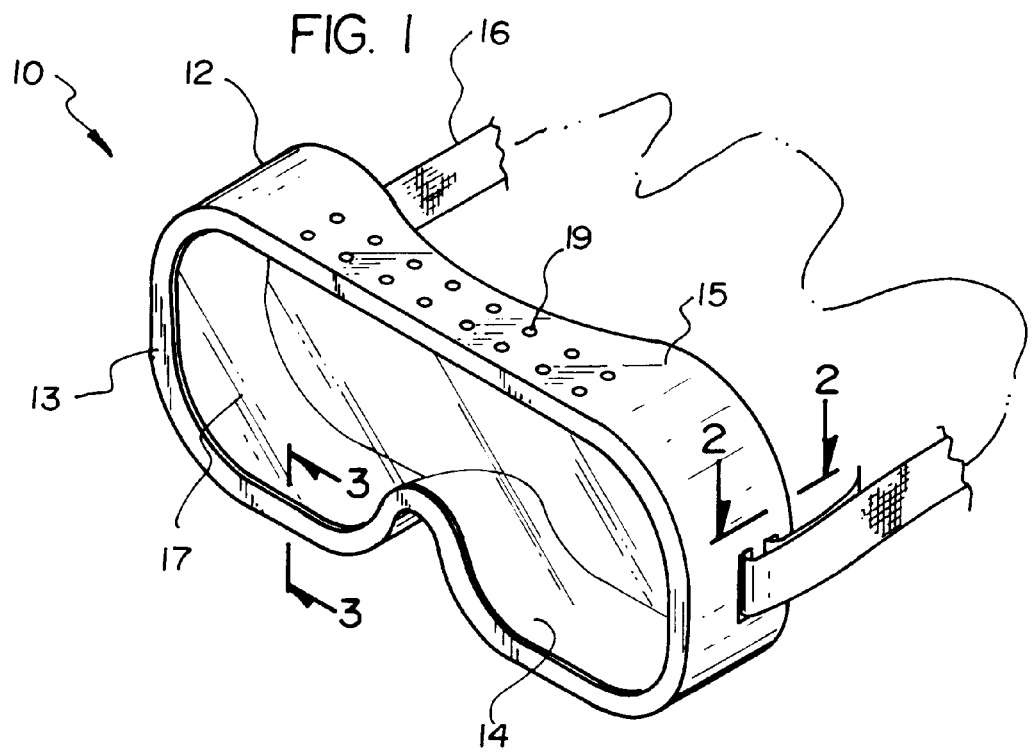
FIG. 1 is a schematic perspective view of a new goggles according to the present invention with a transparent eye shield covering the central space of the frame.
Figure 2:
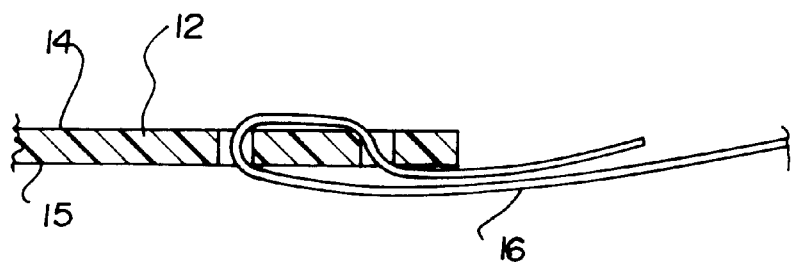
FIG. 2 is a schematic sectional view of the present invention taken from line 2—2 on FIG. 1.
Figure 3:
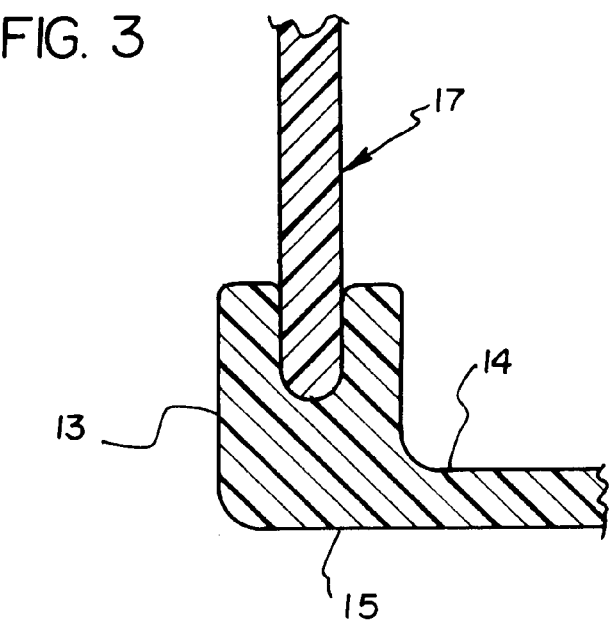
FIG. 3 is a schematic sectional view of the frame and eye shield of the present invention as seen from line 3—3 on FIG. 1.
Figure 4:
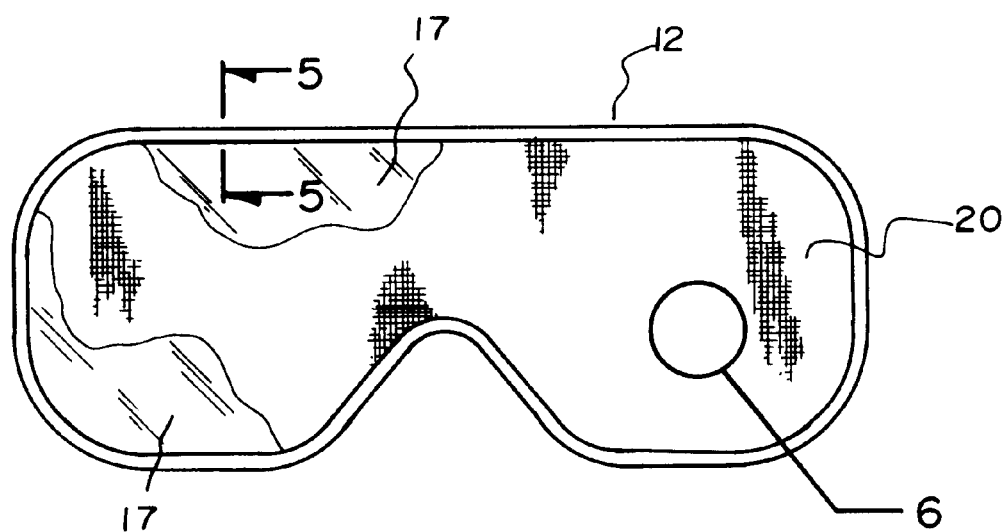
FIG. 4 is a schematic front view of an optional embodiment view of the present invention with a mesh screen eye shield and transparent eye shield.
Figure 5:
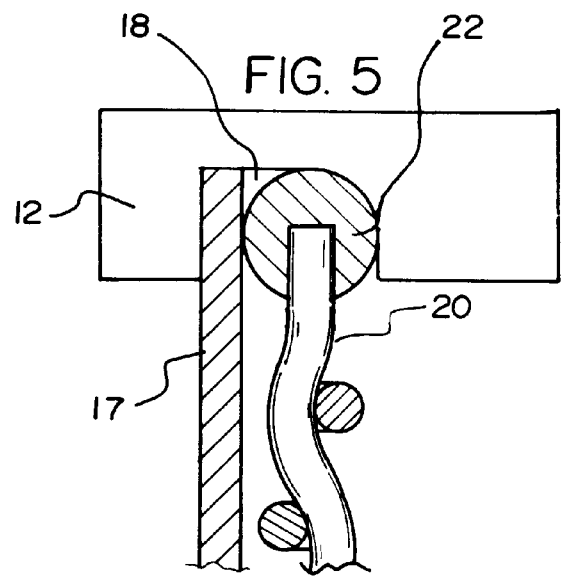
FIG. 5 is a cross-sectional view of the mesh screen eye shield and transparent eye shield of the optional embodiment of the present invention taken from line 5—5 on FIG. 4.
Figure 6:
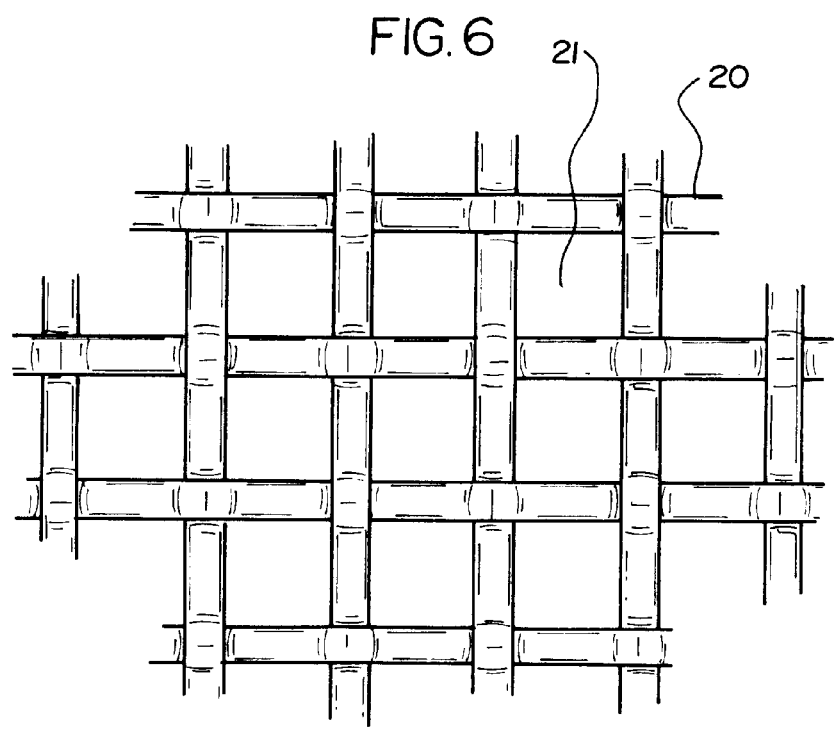
FIG. 6 is a schematic close up view of the mesh screen of the present invention as seen from the vantage of the circle 6 on FIG. 4.

With reference now to the drawings, and in particular to FIGS. 1 through 6 thereof, a new goggles embodying the principles and concepts of the present invention and generally designated by the reference numeral 10 will be described.

As best illustrated in FIGS. 1 through 6, the goggles 10 generally comprises a frame 12 shaped to fit on the face of a wearer and having a front 13 and inner and outer surfaces 14,15. The inner surface 14 of the frame 12 defines a central space. The frame may also have vent holes 19 therethrough. The ends of a flexible strap 16 are coupled to the frame 12. The flexible strap 16 is adapted for looping around the back of the head of a wearer to hold the frame 12 to the face of the wearer. A mesh screen eye shield 20 substantially covers the central space at the front 13 of the frame 12. The mesh screen eye shield 20 has a plurality of generally uniform apertures 21 therethrough. Each of the apertures 21 has a predetermined area and is designed for preventing objects greater than the predetermined sized passing therethrough. The apertures 21 of the mesh screen eye shield 20 are also designed for permitting the passage of moisture therethrough.

Specifically, the frame 12 shaped to fit on the face of a wearer. The frame 12 has a front 13 and inner and outer surfaces 14,15. The inner surface 14 of the frame 12 defines a central viewing space. The inner surface 14 of the frame 12 preferably has an annular channel 18 extending therearound. The channel 18 is positioned adjacent the front 13 of the frame 12. Preferably, the portion of the frame 12 adjacent the channel 18 is flexible to permit insertion and removal of an eye shield 17,20 into the channel 18. The ends of an adjustable flexible strap 16 is coupled to the back of the frame 12. The flexible strap 16 is adapted for looping around the back of the head of a wearer to hold the frame 12 to the face of the wearer.

A fine mesh wire screen eye shield 20 substantially covers the central space at the front 13 of the frame 12. The mesh screen eye shield 20 has mesh screen portion and an generally rigid outer perimeter portion 22. The outer perimeter portion 22 of the mesh screen eye shield 20 is removably inserted into the channel 18 of the inner surface 14 of the frame 12 such that the mesh screen eye shield 20 is held to the frame 12. The mesh screen portion of the mesh screen eye shield 20 has a plurality of generally uniform apertures 21 therethrough. These apertures 21 each has a predetermined area dimension and is designed for preventing objects greater than the predetermined sized passing therethrough. The predetermined size of the apertures 21 is also sufficiently large enough to permit a wearer to see through the mesh screen eye shield 20. The apertures 21 are preferably generally rectangular and each has an area of less than about 4 mm$^2$. Ideally, each of the apertures 21 of the mesh screen eye shield 20 has an area between about 1 mm$^2$ and 4 mm$^2$. Optionally, the wires forming the mesh screen are coated with a black colored coating to help reduce the glare from light passing through the mesh screen. The apertures 21 of the mesh screen eye shield 20 are also designed for permitting the passage of moisture therethrough.

In the preferred embodiment, a generally transparent eye shield 17 may also be provided with the goggles. The transparent eye shield is removably insertable into the channel 18 of the inner surface 14 of the frame 12 such that the transparent eye shield 17 is held to the frame 12 when the transparent eye shield 17 is inserted into the channel 18. Ideally, the transparent eye shield 17 comprises a transparent plastic.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. Goggles, comprising:

a frame shaped to fit on the face of a wearer, said frame having a front and inner and outer surfaces, said inner surface of said frame defining a central space, wherein the frame has a plurality of vent holes formed in a top face thereof;

said inner surface of said frame having a channel extending therearound, said channel being positioned adjacent said front of said frame, a portion of the frame adjacent the channel being flexible;

a flexible adjustable strap having a pair of ends, said ends of said flexible strap being coupled to said frame, said flexible strap being adapted for looping around the back of the head of a wearer to hold said frame to the face of the wearer;

a generally transparent eye shield being removably insertable into said channel of said inner surface of said frame such that said transparent eye shield is held to said frame when said transparent eye shield is inserted into said channel, said transparent eye shield comprising a transparent plastic;

a mesh wire screen eye shield substantially covering said central space at said front of said frame, said mesh wire screen eye shield having a mesh screen portion and a rigid outer perimeter portion having a substantially circular cross-section with a radially extending groove for receiving the mesh screen portion, said outer perimeter portion of said mesh wire screen eye shield being removably inserted into said channel of said inner surface of said frame such that said mesh wire screen eye shield is held to said frame; and said mesh wire screen eye shield having a plurality of generally uniform apertures therethrough, said apertures having a predetermined area and being for preventing objects greater than said predetermined size from passing therethrough, said apertures of said mesh wire screen eye shield being for permitting the passage of moisture therethrough, said predetermined area of said apertures being sufficiently large enough to permit the wearer to see through the mesh screen eye shield, wires of said mesh wire screen eye shield being coated with a black colored coating to reduce glare from light passing through the mesh screen portion, said apertures being generally rectangular and each having an area of less than about 4 $mm^2$, wherein each of said apertures of said mesh wire screen eye shield having an area between about 1 $mm^2$ and 4 $mm^2$.

* * * * *